United States Patent [19]

Matsukawa et al.

[11] 3,965,033

[45] *June 22, 1976

[54] PROCESS FOR THE PRODUCTION OF OIL-CONTAINING MICROCAPSULES

[75] Inventors: Hiroharu Matsukawa; Keiso Saeki, both of Shizuoka, Japan

[73] Assignee: Fuji Photo Film Co., Ltd., Minami-ashigara, Japan

[ * ] Notice: The portion of the term of this patent subsequent to Apr. 9, 1991, has been disclaimed.

[22] Filed: Jan. 31, 1974

[21] Appl. No.: 438,518

Related U.S. Application Data

[63] Continuation-in-part of Ser. No. 166,563, July 27, 1971, Pat. No. 3,803,045.

[30] Foreign Application Priority Data

July 27, 1970 Japan.............................. 45-65650
July 31, 1970 Japan.............................. 45-66894

[52] U.S. Cl.................. 252/316; 252/188.3 R; 264/4; 424/37; 426/89; 426/102; 428/307
[51] Int. Cl.².......................................... B01J 13/02
[58] Field of Search............... 252/316; 117/100 A, 117/62.2; 264/4; 427/338

[56] References Cited
UNITED STATES PATENTS

| | | | |
|---|---|---|---|
| 2,800,457 | 7/1957 | Green et al. | 252/316 |
| 2,886,445 | 5/1959 | Rosenthal et al. | 426/89 X |
| 2,969,331 | 1/1961 | Brynko et al. | 252/316 |
| 3,069,370 | 12/1962 | Jensen et al. | 252/316 X |
| 3,803,045 | 4/1974 | Matsukawa et al. | 252/316 |

FOREIGN PATENTS OR APPLICATIONS 929,405  6/1963  United Kingdom............... 252/316

*Primary Examiner*—Richard D. Lovering
*Attorney, Agent, or Firm*—Sughrue, Rothwell, Mion, Zinn & Macpeak

[57] ABSTRACT

In a process for producing oil-containing microcapsules by coacervation comprising
a. introducing a fine powder or hydrophobic liquid into a high molecular weight electrolytic wall-forming colloid;
b. coacervating the resulting dispersion or emulsion;
c. cooling the resulting coacervate to gel it and form the wall of said microcapsules; and
d. hardening said wall of said microcapsules; the improvement which comprises adding a phenolic compound to the system.

19 Claims, No Drawings

PROCESS FOR THE PRODUCTION OF OIL-CONTAINING MICROCAPSULES

CROSS REFERENCE TO RELATED APPLICATIONS

This application is a continuation-in-part of copending U.S. application Ser. No. 166,563 Matsukawa et al, filed July 27, 1971, now U.S. Pat. No. 3,803,045 and entitled "Process for the Production of Oil-Containing Microcapsules."

BACKGROUND OF THE INVENTION

1. Field of the Invention

The present invention relates to a process for producing oil-containing microcapsules, and more particularly to a process for microencapsulating an oily liquid by coacervation utilizing gelatin as at least one of the hydrophilic colloids, whereby oil-containing microcapsules, whose walls are less porous and thicker, can be obtained without aggregation.

2. Description of the Prior Art

The process of producing microcapsules by coacervation has hitherto been described in U.S. Pat. Nos. 2,800,457 and 2,800,458, and is classified into simple coacervation or complex coacervation depending upon the liquid-liquid phase separation of the colloid of the hydrophilic high molecular weight electrolyte.

The term, "liquid-liquid phase separation" is intended to cover such an operation that a solution of one or more kinds of high molecular weight electrolyte colloids is separated into two different liquid phases, i.e. a colloid-rich phase and a colloid-poor phase, and such phase separation phenomenon is usually termed "coacervation". The colloid-rich phase which is obtained by the phase separation is called the "coacervate", and when the thus obtained coacervate is composed of a single kind of colloid, the operation is called simple coacervation and, when composed of two or more kinds of colloids, the operation is called complex coacervation.

Microcapsules have the following advantages:
1. the liquid is outwardly in the form of a solid,
2. two or more kinds of reactive materials can be preserved for a long term in the form of a mixture because they are isolated with the wall,
3. a liquid in which a solid material may be dissolved has the capability of protecting the material included therein from the environment and stored for a desirable term,
4. color, taste or toxicity can be intercepted,
5. the release of liquid in which a solid substance may be dissolved can be controlled,
6. the liquid can be maintained on a plane, and
7. handling of the liquid is easy.

Therefore, applications thereof to agricultural chemicals, chemicals, medicine, perfumery, adhesives, liquid crystal, paint, foods, detergents, dyes, solvents, catalysts, enzymes, anticorrosives and the like have been studied. Especially, aspirin-containing capsules, perfumery-containing capsules, menthol tobacco, pressure-sensitive adhesive capsules, reaction type adhesive capsules, color-former containing capsules for pressure-sensitive recording paper, anticorrosive-containing capsules for rivets are manufactured industrially.

While various microencapsulating methods have been proposed for these purposes, the coacervation process is the most useful. The process of forming microcapsules according to coacervation is suitable for microencapsulating a liquid droplet itself or a liquid droplet containing a material dissolved or dispersed therein, but controlling the various conditions therefor is difficult. Namely, the formation of the coacervate according to a simple coacervation is influenced by the colloid concentration, salt concentration, proportion of colloid to the material to be microencapsulated, the stirring state of the system, the temperature of the system and the like; and the formation of the complex coacervate is influenced by the colloid concentration, the colloid ratio, the pH of the system, the temperature of the system, the proportion between the colloid and the material to be microencapsulated, the stirring state of the system, properties of the colloids used, and the like. In these conditions for coacervations, there are, of course, optimum conditions.

Accordingly, as the system is slipped out from the optimum conditions, the coacervation is insufficiently carried out and less of the coacervate is produced. For example, when the concentration of the colloid is low, the coacervation is sufficiently carried out whereby the production of coacervate is increased, and if the concentration of colloid is high, the coacervation is insufficiently carried out and less of the coacervate is produced.

Since gelatin is used as one of the colloids for improving the thermal properties of the wall (for example, the wall is not melted at a temperature higher than 70°C) and a hardening agent such as formaldehyde is used for hardening gelatin, it is further difficult to carry out the process.

Such formation of microcapsules by the utilization of the coacervation process has various demerits such as (a) complicated establishment of the conditions for forming the coacervate, (b) necessity of gelatin as at least one kind of wall membrane-forming colloid, (c) requirement of treatment for imparting a high heat-resistance to the wall membrane and (d) undesirable limitations in the process and in the shape of the formed microcapsule.

Typical limitations in the process are based on the following items:

An operation of concentrating the capsules is required because the colloid concentration for producing the capsule is limited to 2.5% (a main reason of limiting the concentration is depending upon preventing aggregation of the capsules owing to the elevation of viscosity in the system when rapidly converting the pH to harden the coacervate), there is a large difference in the slurry viscosity because gelatin is not deposited around the liquid to be encapsulated and remained in the system, and to hardening the wall of gelatin, pH is not rapidly converted to alkalinity.

The limitation on the shape of the formed microcapsules is based on the following items:

Grape-like capsules (hereinafter, referred to as "poly nucleus capsule"), which are numerous aggregated droplets, are produced due to the limitation of the colloid concentration, a porous wall is formed and the strength of the wall becomes the same as that property of the gelatin because most of the negative electrolytic colloid having an electric charge opposite to the gelatin is pulled out into the system equilibrium solution at the step of completing formation of the capsule, and the viscosity of the slurry is increased and the thus formed microcapsules are aggregated in the step of changing the pH to the alkali side because the microcapsules are formed with high concentration of colloid and hardened.

An important aspect of the present invention is to improve the foregoing limitations, to rapidly adjust the pH of the slurry to the alkali side in the presence of a hardening agent for preventing elevation of the viscosity, stabilizing and hardening the wall at the step of making the capsule in a higher colloid concentration, to control proper sizes of microcapsules containing one liquid droplet (hereinafter, referred to as "mono nucleus capsule") or polynucleus capsules and to reduce the porosity of the wall thus prepared.

That is to say, the process of the present invention provides a practical multi-useful process on an industrial scale.

SUMMARY OF THE INVENTION

The above objects can be attained by adding a phenolic compound to the system for producing microcapsules at a temperature higher than 5°C, preferably higher than 8°C, namely, before hardening pretreatment. When the process is conducted under insufficient coacervation conditions, more effective results are obtained.

DESCRIPTION OF THE PREFERRED EMBODIMENTS

The insufficient conditions used in the present invention and the merits of the present invention will be set forth as follows:
  a. Since the formation of capsules can be achieved in a higher colloid concentration, a large quantity of the capsules can be produced and therefore, production costs can be reduced, and the amount of coater to be evaporated is small, whereby thermal means and apparatus therefor are more simple.
  b. A liquid to be encapsulated is effective to the amount of colloid.
  c. All steps of the above process are continuously conducted because the elevation of the viscosity is not caused and the step for hardening the system does not become the velocity controlling step, and the load for the stirrer is reduced.

As described above, the process of the present invention has numerous merits and remarkable improvements in practical operation.

The phenolic compound used in the present invention may be a phenol monomer or a phenol resin.

The typical phenol monomer used in the present invention is an aromatic compound of which the hydrogen atom attached to the ring, is substituted with at least one hydroxyl group. The examples include substituted phenols, polyhydric phenols, phenol carboxylic acids, nitrophenols, biphenols and the like. They may usually be used as a solution dissolved in water or an alcohol.

As examples of the substituted phenols, there are phenol compounds having, as the substituent, an alkyl, an allyl, a halogen, a halogen-substituted alkyl, a cycloalkyl, a phenyl, a halogen-substituted phenyl, an alkyl-substituted phenyl, biphenyl, benzyl and α-alkylbenzyl groups.

The process of the invention should not be limited even if the compound is substituted with one or more of the above substituents.

Further examples of substituted phenols are o-cresol, m-cresol, p-cresol, o-ethylphenol, p-tert-butylphenol, p-nonylphenol, p-dodecylphenol, p-octylphenol, p-fluoro-phenol, p-chlorophenol, p-bromophenol, m-chlorophenol, p-cyclo-hexylphenol, o-phenylphenol, p-phenylphenol, o-(o-chlorophenyl)-phenol, p-(p-bromophenyl)-phenol, o-(2-biphenylyl)-phenol, α-phenyl-o-cresol, 2,4-xylenol, 3,4-xylenol, 2-allyl-p-cresol, 2,4-dichlorophenol, 2,5-dichlorophenol, 4-chloro-m-cresol, 2-chloro-4-phenylphenol, 2,3,5-trimethylphenol, 2,3,5,6-tetramethylphenol, α-naphthol, β-naphthol and the like.

As examples of polyhydric phenols, there are resorcinol, catechol, hydroquinone, pyrogallol, fluoroglucinol, 1,2-dihydroxy-4-methylbenzene, 1,3-dihydroxy-5-methylbenzene, 3,4-dihydroxy-1-methylbenzene, 3,5-dihydroxy-1-methylbenzene, 2,4-dihydroxyethyl-benzene, tert-butylhydroxyquinone, 1,3-naphthalenediol, 1,4-naphthalenediol, 1,5-naphthalenediol, 1,6-naphthalenediol, 1,7-naphthalenediol, 4-phenylpyrocatechol, 4-chloroesorcinol, phenyl-hydroquinone, 4,6-dichloroesorcinol, tetrachlorohydroquinone and the like.

As examples of phenol carboxylic acids, there are m-oxybenzoic acid, p-oxybenzoic acid, protocatechuic acid, α-resorcylic acid, β-resorcylic acid, orsellinic acid, caffeic acid, umbellic acid, gallic acid and the like. As the nitrophenols, there are, for example, p-nitrophenol, m-nitrophenol, o-nitrophenol and the like.

Examples of the biphenols include biphenol, bicresol, dibenzylbiphenol, diethylbiphenol, dipropylbiphenol, diallylbiphenol, dihalobiphenol, biphenyltetrol, methylenediphenol, methylenebis(alkylphenol), methylenebis(benzylphenol), methylene(phenylphenol), methylenebis(halophenol) and the like.

As the biphenol type compound, there are, for example, o,o'-biphenol, m,m'-biphenol, p,p'-biphenol, 4,4'-bi-o-cresol, 4,4'-bi-m-cresol, 6,6'-o-cresol, 2,2'-diethyl-p,p'-biphenol, 2,2'-diallyl p,p'-biphenol, 3,3', 5,5'-biphenyltetrol, 4,4'-methylenediphenol, 2,4'-methylenediphenol, 2,2'-methylenediphenol, 4,4'-isopropylidenediphenol, 4,4'-cyclopentylidenephenol, 4,4'-cyclohexylidene-diphenol, methylenediresorcinol, 4,4'-methylene-di-o-cresol, 4,4'-methylenebis(2-chlorophenol), 4,4'-methylenebis(2,5-dichlorophenol), 4,4'-thiodiphenol and the like. The above phenol monomers may also be used in the form of their sodium or potassium salts.

The typical examples of the phenolic resin used in the present invention include phenol-aldehyde condensates which, in general, are called resol types or novolak types.

A water-soluble type of the phenolic resin is more suitable for the process of the present invention, but a so-called alcohol-soluble novolak type can also be used after dissolving it in a water-compatible solvent.

The raw materials for producing the phenolic resins used in the present invention are phenols and aldehydes. As the phenols thereof, there are, for example, phenol, cresol, xylenol, alkylphenols, resorcinol, etc., and as the aldehydes, there are, for example commercially available 37 wt. % formalin, p-formaldehyde, etc. The resol type phenolic resin is obtained by reacting 1.0 mole or more of formaldehyde with 1 mole of phenol in the presence of sodium hydroxide or tertiary amine. On the other hand, the novolak type phenolic resin can usually be prepared by reacting 1 mole or less of formaldehyde with 1 mole of phenol in the presence of an inorganic acid such as hydrochloric acid or surfuric acid, or an organic acid such as oxalic acid. And also, there is used ammonia-resol which is prepared by using ammonia as the catalyst. Various kinds of phenolic resins have been commercially prepared by the foregoing procedure in industrial scale, and can be easily obtained.

The process of the invention is conducted by the coacervation caused by the dilution with water and the addition of salt or pH adjustment.

The following procedure will be set forth to exemplify the process of the present invention, that is,
1. dispersing a hydrophobic fine powder or emulsifying a hydrophobic liquid into an aqueous solution of at least one kind of high molecular weight electrolytic colloid which is used for forming the capsule wall (dispersing or emulsifying step);
2. subjecting the dispersion or the emulsion obtained in step (1) to water dilution, and then salt addition and/or pH adjustment thereof. In this case, an aqueous solution of a high molecular weight colloid may be added thereto, if desired (coacervation step);
3. cooling the formed coacervate to gel it (cooling step);
4. adding a phenolic compound thereto at a temperature of above 5°C, preferably above 8°, during the steps of (2) and (3);
5. adding a hardening agent to the system;
6. adding a shock-preventing agent at a temperature lower than the gelling point of gelatin; wherein by "shock" is meant such a phenomenon that the viscosity of the system elevates rapidly, i.e., at a pH not less than near (about) 6, generally at a pH not less than near 6 to 13 and not commonly at a pH of not less than near 6 to 9, when conducting the pre-hardening of the coacervation capsule liquid containing the gelatin, and by "shock-preventing agent" is meant a solution for prevening the shock;
7. adjusting the pH of the system to the alkali side (the foregoing steps (5), (6) and (7) (pre-hardening treatment); and
8. optionally elevating the temperature of the system to more effectively harden the coacervate (hardening step).

In the above method, the order of steps (5), (6) and (7) can freely be modified with respect to each other, and step (5) may also be conducted prior to step (4).

In the above procedure, even though the phenolic compound may be added to the system without using a prehardening treatment, some results are obtained, but, when the compound is added to the system at the step (4) and the shock-preventing agent is added at the prehardening treatment, more excellent results can be obtained. The above order is only an embodiment of the invention, and the process is not limited thereto. For example, both the phenolic compound and the shock-preventing agent can be simultaneously added a temperature lower than the gelling point of gelatin and higher than 5°C, preferably higher than 8°C.

Examples of the hydrophilic colloids include gelatin, casein, alginate, gum arabic, carrageenan, maleic acid-styrene copolymer, maleic acid-methyl vinyl ether copolymer, maleic acid-ethylene copolymer and the like. In the process of the present invention, gelatin must be used as one of the hydrophilic colloids.

As the nucleus of the capsule, there are, for example, natural oils such as mineral oils, animal oils or vegetable oils, synthetic oils, hydrophobic fine particles and the like.

The typical examples of the hardening agents include formaldehyde, acetaldehyde, glyoxal, glutaldehyde, chrome alum and the like.

As the shock-preventing agents, there are those compounds having anionic functional groups, for example, cellulose derivatives, such as carboxymethyl cellulose, carboxyethyl cellulose, sulfated cellulose, phosphorated cellulose, carboxymethylhydroxyethyl cellulose, etc.; starch derivatives such as carboxymethyl starch, sulfated starch, phosphorated starch, etc.; D-galacturonic acids such as pectin, pectinic acid, etc.; vinylbenzenesulfonic (or sulfonate) copolymers such as vinylbenzenesulfonate-acryloyl-morpholine copolymers, vinylbenzenesulfonate-acrylamide copolymers, vinylbenzenesulfonate-vinylpyrolidone copolymers, etc.; and acrylic acid (salt) copolymers such as acrylic acid-acryloylmorpholine copolymers, acrylic acid-vinylpyrrolidone copolymers, etc. The shock-preventing agents are disclosed in German OLS No. 1,939,624, which is the equivalent of U.S. Pat. No. 3,687,865, Katayama et al, hereby incorporated by reference.

As disclosed in U.S. Pat. No. 3,687,865 Katayama, et al., shock preventing agents which may be used are polyelectrolytes having an anionic functional group. As examples of such polyelectrolytes may be mentioned modified cellulose, an anionic starch derivative, an anionic acid polysaccharide, a condenstate of naphthalene sulfonic acid and Formalin, a hydroxyethyl cellulose derivative, a copolymer of vinylbenzene sulfonate and a copolymer of sodium acrylate, a maleic acid copolymer of maleic acid anhydride and at least one monomer having at least one unsaturated bond which is subjected to addition polymerization with said anhydride or a salt thereof, and a nucleic acid compound.

As examples of modified cellulose, there may be mentioned polysaccharides having $\beta$-1,4-glucoside bonds of glucose and having anionic functional groups. Part or all of the hydroxyl groups of the cellulose may be etherified or esterified. Illustrative of cellulose ethers are carboxymethyl cellulose, carboxyethyl cellulose and metal salts thereof, and illustrative of cellulose esters are cellulose sulfate, cellulose phosphate and metal salts thereof.

The anionic starch derivative may be one which is composed of a linear polysaccharide amylose formed by only $\alpha$-1,4 bonds of D-glucose, and a branched polysaccharide amylopectin formed by mainly $\alpha$-1,4 bonds of D-glucose and partially side chain branched by $\alpha$-1,6 bonds.

As examples of the above starch derivatives may be mentioned carboxymethyl starch, carboxyethyl starch, starch sulfate, starch phosphate and starch xanthate. These are obtained by etherification or esterification of corn starch, wheat starch, rice starch, potato starch, sweet potato starch or tapioca starch, which may be extracted from either the seeds or the roots of the plants in high yield.

As examples of the anionic acid polysaccharides, there may be mentioned polygalacturonic acid, which is obtained by polycondensating linearly D-galacturonic acid between $\alpha$-1,4-bonds thereof. The acid polysaccharide contains pectin, pectic acid and pectinic acid. These are basic substances comprising pectin matter in a high plane and have been defined as follows:

pectinic acid - polygalacturonic acid in the colloid form containing some methyl ester groups pectin - water soluble pectinic acid containing methyl ester groups.

The condensate or naphthalene sulfonic acid and Formalin is represented by the following formula:

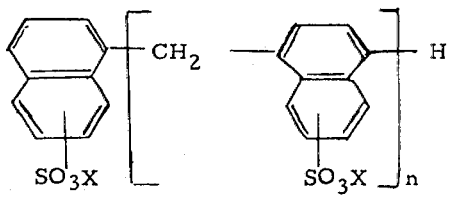

wherein X is a hydrogen atom, an alkali metal or an ammonium group, and $n$ is a positive integer.

Shock-preventing ability of the above condensate is influenced by the degree of polymerization, and it is preferably that $n$ be 5 to 9. In general, the larger the larger the value of $n$, the more water-solubility and viscosity increases. These compounds are described in Kogyo Kagaku Zashi 66 [1], pp. 55–69 (1963).

As examples of the hydroxyethyl cellulose derivatives, there may be mentioned carboxymethyl ether of hydroxyethyl cellulose, hydroxyethyl cellulose sulfate and hydroxyethyl cellulose phosphate and the like.

As examples of the copolymers of vinylbenzene sulfonate, there may be mentioned vinylbenzene sulfonateacryloylmorpholine copolymer, vinylbenzene sulfonatemorpholinomethylacrylamide copolymer, vinylbenzene sulfonate acrylamide copolymer, vinylbenzene sulfonatevinylpyrrolidone copolymer, and vinylbenzene sulfonatemethoxymethylacrylamide.

The polymers contain the following group in the molecule:

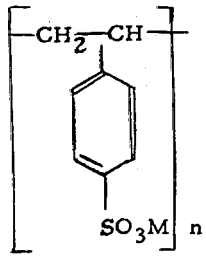

wherein M is an alkali metal and $n$ is a positive integer. The amount of vinylbenzene sulfonate in the copolymer is preferably 45–95 mol percent, more preferably 60–85 mole percent, and it is preferred, for the purpose of this invention, to use a copolymer having a molecular weight of 10,000–3,000,000 particularly 100,000–1,000,000.

As examples of copolymers of acrylic acid, there may be mentioned acrylic acid-acryloylmorpholine copolymer, acrylic acid-morpholinomethylacrylamide, acrylic acidacrylamide copolymer, acrylic acid-vinylpyrrolidone copolymer, and acrylic acid-methoxymethylacrylamide.

These polymers contain the following group:

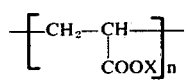

wherein X is a hydrogen atom or an alkali metal, and $n$ is a positive integer.

The amount of acrylic acid in the copolymer is preferably in 40–95 mol percent, especially 50–85 and it is preferable for the purposes of this invention, to use a copolymer having molecular weight of 6,000–2,000,000, especially 50,000–1,000,000.

Examples of preferred maleic acid copolymers are copolymers of maleic acid anhydride and at least one monomer selected from a group consisting of acrylic acids, methacrylic acids, vinyl ethers, styrenes and olefins such as styrene, methylvinyl ether, ethylene, isobutylene, and terpolymers with styrene and acrylic butyl ester. Examples of preferred salts thereof are alkali metal salts (e.g., Na, K, etc) and amine salts (e.g. ammonium salt, etc.).

Examples of preferred nucleic acid compounds are sodium salts of nucleic acids.

The amount of the phenolic compound is 1/500 to ¾ part by weight, preferably, 1/100 to ½ part by weight based on 1 part by weight of gelatin used to form the capsule wall.

The viscosity-variation of the hitherto known coacervation process is compared below with that of the process of the present invention comprising using the phenolic compound.

In both processes, a system (coacervation pH:4.5) containing 11 parts by weight of colloid (6 parts of gelatin and 5 parts of gum arabic) in 210 parts by weight of water was used respectively. In the practice of the process of the present invention, resorcinol or a mixture of resorcinol and a shock-preventing agent (carboxymethyl cellulose) was added thereto at a temperature of 30°C.

|  | U.S.P. No. 2,800,457 | Addition of resorcinol | Addition of resorcinol and shock-preventing agent |
| --- | --- | --- | --- |
| Deposited amount of gelatin | 76% | 85% | 85% |
| Viscosity at 10°C | 84 cp | 42 cp | 42 cp |
| Maximum viscosity during dropping alkali | 6700 cp | 2500 cp | 55 cp |

As is clear from the foregoing results, in the process of forming capsules comprising combining the water-dilution with the pH adjustment as described in U.S. Pat. No. 2,800,457, the addition of resorcinol, which is one of the phenolic compounds of the present invention, makes the increase of deposited amount of the gelatin remarkable and makes the production of microcapsules having thick walls and a lower porosity possible. And also, the viscosities at 10°C and during the pH adjustment is lowered to ½ that achieved by the conventional process.

Especially, when the phenolic compound is used together with the shock-preventing agents, elevation of the viscosity during the pH-adjustment is remarkably lowered and mononuclear capsules having better heat-resistance can be efficiently produced. As mentioned above, the process of the present invention is useful for producing microcapsules and is applicable conveniently to the processes of microencapsulating a color former for a pressure-sensitive copying paper, perfumery, an adhesive, a catalyst, chemicals, a medicine and the like.

The process of the present invention will be further understood by the following specific examples, but it is not limited to them.

The term, "part" in all examples means "part by weight", and "viscosity" represents "cp. (centipoise)" determined by means of B type rotary viscometer (manufactured by Tokyo Keiki Co., Ltd.).

EXAMPLE 1

In 25 parts of water (35°C), 6 parts of acid-treated gelatin having an isoelectric point of 8.2 and 6 parts of gum arabic were dissolved. Then, 30 parts of chlorinated diphenyl in which 2.0% of crystal violet lactone and 2.0% of benzoyl leucomethylene blue were dissolved was added into the colloid solution and emulsified with vigorous stirring to form an oil in water type emulsion. When the drop size became 6 to 10 $\mu$, the stirring was stopped, and then 170 parts of warm water at 35°C were added thereto.

Thereafter, 10 parts of a 5% aqueous resorcinol solution was added thereto while stirring, and the pH was adjusted to 4.4 with 50% acetic acid. Then the contents were cooled, with stirring, out of the vessel to gel the colloid wall, and when the temperature was 15°C, with stirring, 2.5 parts of 37% formaldehyde was added thereto. Further, 15 parts of a 10% aqueous solution of carboxymethyl cellulose (degree of etherification: 0.73, average degree of polymerization: 220) was added thereto when the temperature of the system was 10°C (the viscosity of the capsule solution at 10°C was 35 cp), and the pH was then adjusted to 10.0 with 10% caustic soda.

The dropping time (of the caustic soda) was 5 minutes, and the viscosity at pH 8.0 was 48 cp. Subsequently, the system was heated to 50°C to harden the wall. The so-obtained capsules were mostly single nucleus capsules, and the dried capsules showed little release of the nucleus included therein in a deterioration test of heating to 100°C for 10 hours. The capsules obtained in this Example could be effectively utilized in pressure-sensitive copying paper. After the given capsule solution was coated onto a base paper of 40 g/m$^2$ and dried, it was contacted with a commercially available clay-coated paper for a pressure-sensitive copying paper and written on to obtain a distinct blue color image on the clay-coated paper.

COMPARATIVE EXAMPLE 1

The same procedure as in Example 1 was repeated except that neither resorcinol nor carboxymethyl cellulose as the shock-preventing agent were used.

The capsule dispersion aggregated during the addition of alkali. The viscosity at pH 8.0 was over 3000 cp and the diameter of the capsules was about 200 millimeters.

COMPARATIVE EXAMPLE 2

The same procedure as in Example 1 was repeated except that resorcinol was not used. The viscosity at 10°C was 98 cp and that at pH 8.0 during the dropping of alkali was 205 cp.

EXAMPLE 2

In 20 parts of warm water at 35°C, 6 parts of acid-treated gelatin having an isoelectric point of 8.2 was dissolved. Then, 35 parts of lemon oil were added thereto and emulsified to prepare an oil in water type emulsion. When the oil droplets became 20–25 $\mu$ in size, the stirring was stopped and 6 parts of gum arabic dissolved in 180 parts of warm water at 35°C was then poured therein, then the pH was adjusted to 4.2 by dropping 10% hydrochloric acid therein with stirring. The contents were cooled, out of the vessel, with stirring, to gel the deposited colloid wall. When the temperature of the system was 25°C, during the cooling step, 10 parts of an 5% aqueous catechol solution was added, and when the temperature was 10°C, 20 parts of a 10% sodium sulfated cellulose (degree of esterification: 0.74, viscosity in 2% aqueous solution at 25°C: 64 cp) was added thereto and further 3.0 parts of 37% formaldehyde was poured therein (viscosity at 10°C: 20 cp). Subsequently, the pH was adjusted to 9.5 by dropping 10% caustic soda therein and the viscosity at pH 8.0 was 36 cp. Then, the solution was heated to 45°C to obtain good heat resistant single nucleus capsules containing lemon oil.

EXAMPLE 3

In warm water at 37°C, 6 parts of acid-treated gelatin having an isoelectric point of 8.2, 4 parts of gum arabic and 0.5 parts of methylvinyl ethermaleic acid copolymer (Trade Name, Gantrez AN-119 A, manufactured by General Aniline & Film Corp.) were dissolved.

Then, 0.1 part of Turkey oil was added thereto. Subsequently, 30 parts of chlorinated paraffin was emulsified. When the size of the formed oil in water type emulsion became 10–15 $\mu$, 150 parts of warm water at 35°C was poured therein. And, 0.5 part of pyrogallol was added thereto with gentle stirring of the system. After adding 25 parts of warm water at 35°C thereto, the pH was then adjusted to 4.5 by pouring 10% sulfuric acid therein. The contents were cooled, out of the vessel, to gel the wall.

When the temperature was 10°C, 20 parts of 10% phosphorated starch sodium salt (degree of esterification: 0.65, viscosity at 20°C: 210 cp) was added and the pH was then adjusted to 9.2 by the dropping of 10% caustic soda therein. Further, 3.0 parts of 37% formaldehyde was added dropwise thereto. And then, the system was heated to 45°C to obtain a capsule having a hardened wall. The viscosity at 10°C during the preparation of said capsule was 47 cp and the maximum viscosity during dropping of formaldehyde was 117 cp.

COMPARATIVE EXAMPLE 3

The same procedure as in Example 3 was repeated except that pyrogallol was not used. The viscosity at 10°C during the preparation of the capsule was 73 cp and the maximum viscosity during dropping of formaldehyde was 183 cp.

EXAMPLE 4

In 30 parts of warm water at 35°C, 6 parts of acid-treated gelatin having an isoelectric point of 8.2, 5 parts of gum arabic and 0.2 part of polyacrylic acid (Trade Name: 1OH, manufacture by Toa Gosei Chemical Industry Co., Ltd.) were dissolved.

Then, 20 parts of an epoxy resin (Trade Name: "Araldite" manufactured by Ciba Limited) was emulsified until the size of emulsion become 50$\mu$.

Thereafter, 180 parts of warm water at 35°C was added thereto, and the pH was adjusted to 4.3 by pouring therein 50% acetic acid. The contents were then cooled, out of the vessel, with stirring of the system. When the temperature of the system was 12°C, 0.5 part of gallic acid dissolved in 5 parts of methanol was added thereto, and when the temperature became 8°C, 25 parts of a 5% aqueous pectinic acid solution and subsequently 3.5 parts of 25% glyoxal were added thereto.

The viscosity at 8°C was 35 cp. Further, the pH was adjusted to 9.5 by the dropwise addition of 10% caustic soda. The viscosity at pH 8.0 was 39 cp. The contents were then heated to 40°C to obtain capsules containing epoxy resin. The so obtained capsules were single nucleus capsules, and could be stored without being ruptured even after being subjected to a deterioration test of heating to 100°C for 10 hours.

Said microcapsules were utilized as adhesive capsules. That is, the dried powder, prepared by a spray-drying process, was dispersed in a polyamine solution and could be stored as one liquid type pressure-sensitive adhesive.

COMPARATIVE EXAMPLE 4

The same procedure as in Example 4 was repeated except that the methanol solution of gallic acid was not used. As a result, the viscosity at 10°C during preparing the capsule was 70 cp and that at pH 8 was 121 cp.

EXAMPLE 5

The same procedure as in Example 4 was repeated except that 0.5 part of gallic acid was replaced by 0.3 part of 4,4'-bis(4-oxyphenyl)sulfone and 5 parts of methanol was replaced by 4 parts. As the result, the viscosity at 10°C was 27 cp and that at pH 8 was 34 cp.

EXAMPLE 6

The same procedure as in Example 1 was repeated except that 5 parts of the methanol solution in which 0.5 part of bisphenol A was dissolved was used instead of 10 parts of a 5% aqueous solution of resorcinol and the former was added thereto at 25°C during the cooling step. As the result, the viscosity at 10°C was 37 cp and that at pH 8 was 42 cp.

EXAMPLE 7

The same procedure as in Example 2 was repeated except that 35 parts of lemon oil, 10 parts of catechol solution and 20 parts of 10% sulfated cellulose sodium salt were replaced by 35 parts of cotton seed oil, 10 parts of a methanol solution in which 0.4 part of p-tert-amylphenol was dissolved and 15 parts of 10% carboxymethylhydroxyethyl cellulose (degree of etherification:

0.52, viscosity in a 2% aqueous solution at 25°C: 185 cp), respectively. As a result, the viscosity at 10°C was 32 cp and that at pH 8.0 was 38 cp.

SYNTHESIS OF PHENOLIC RESIN

Synthesis Example 1

(Synthesis of resol resin from formaldehyde and phenol)

A separable flask of 500 ml. content was equipped with a stirrer, a thermometer, a syphon for sampling specimens.

The syphon was connected with a collecting trap and 94 g (1 mole) of distilled phenol was charged to the flask, to which were added 164 g (2 mole) of a 37% aqueous solution of formaldehyde and 2 g of sodium hydroxide, and then the mixture was heated while stirring for 2 hours at 70°C in an oil bath. After the pH was adjusted to 7.2 with 5% dilute sulfuric acid, the inner pressure was decreased to 30 to 50 mm Hg by means of a tap aspirator.

Thereafter, water was distilled off through a condenser newly equipped for the distillation while paying attention to the temperature being not over 70°C.

Synthesis Example 2

(Synthesis of resol resin from resorcinol and formaldehyde)

A separable flask of 500 ml. content was equipped with a stirrer, a thermometer and a syphon, which was connected with a collecting trap, for sampling a specimen. 110 g (1 mole) of resorcinol, 30 g of distilled water, 123 g (1.5 mole) of a 37% aqueous solution of formaldehyde and 2 g of sodium hydroxide were placed in the flask, and then the mixture was heated while stirring for 3 hours at 80°C in an oil bath. The inner pressure was reduced to 30 to 50 mm Hg by means of a tap aspirator. Thereafter, water was distilled off through a condenser equipped newly for the distillation while paying attention to the temperature being not over 80°C.

Synthesis Example 3

(Synthesis of resorcinol-phenol-formaldehyde condensation copolymer)

Synthesis Example 2 was repeated except that 44 g (0.4 mole) of resorcinol and 56.4 g (0.6 mole) of phenol were used instead of 110 g of resorcinol to obtained a resorcinol-phenol-formaldehyde condensation copolymer.

Synthesis Example 4

(Synthesis of novolak resin from phenol and formaldehyde)

To the same separable flask of 500 ml. content as in Synthesis Example 1 were charged 94 g (1 mole) of phenol, 10 ml. of water, 85.6 g (0.8 mole) of a 37% aqueous solution of formaldehyde and 0.8 g of oxalic acid dihydrate. The mixture was refluxed with stirring for 30 minutes, and further refluxed, after adding 0.8 g of oxalic acid dihydrate thereto, with stirring for 1 hour.

300 ml. of water was then added thereto to cool the resulting mixture and allowed to stand for 30 minutes to precipitate the resin. After water of the upper portion was removed by decantation and the flask was equipped with a condenser for distillation under reduced pressure, the system was initiated to heat, and water was distilled off under a reduced pressure of 50 to 100 mm hg. and when the inner temperature became 110°C, the distillation of water was stopped.

the novolak type resin formed was dissolved in a modified alcohol to give a 40% resin solution.

EXAMPLE 8

In 25 parts of warm water at 35°C, 6 parts of acid-treated gelatin having an isoelectric point of 8.2 and 6 parts of gum arabic were dissolved. Then, 30 parts of chlorinated diphenyl having dissolved therein 2.0% crystal violet lactone and 2.0% benzoyl leucomethylene blue were added into the colloid solution and emulsified with vigorous stirring to form an oil in water type emulsion. When the drop size became 6 to 10 $\mu$ the stirring was stopped, then 175 parts of warm water at 35°C was added thereto.

Thereafter, 1 part (60% resin content) of the phenolic resin obtained in Synthesis Example 1 was added thereto with continuing the stirring, and the pH was adjusted to 4.3 by the dropwise addition of 50% acetic acid. Then, the contents were cooled, with stirring, out of the vessel, to gel the colloid wall, and when the temperature was 18°C, 2.5 parts of a 37% aqueous solution of formaldehyde was added thereto, with stirring of the system. The viscosity when the temperature became 10°C was measured and found to be 28 cp.

Subsequently, 15 parts of a 10% aqueous solution of sodium carboxymethyl cellulose (degree of etherification: 0.73, average degree of polymerization: 220) as a shock-preventing agent was poured therein and the pH was adjusted to 10.0 with the dropwise addition of 10% caustic soda. The dropping time was 3 minutes, and the maximum viscosity during dropping of the alkali was 32 cp and the pH value at that time was 7.9. Thereafter, the system was heated to 50°C to harden the wall. The so obtained capsules were mostly single nucleus capsules, and the dried capsules showed little release of materials included therein during a deterioration test of heating to 100°C for 10 hours. The capsules obtained in this Example could be effectively utilized in a pressure-sensitive copying paper. After the so given capsule solution was applied to a base paper of 40 g/m² and dried, it was contacted with a commercially available clay-coated paper for a pressure-sensitive copying paper and written on to obtain a distinct blue color image on the clay-coated paper.

COMPARATIVE EXAMPLE 5

The same procedure as in Example 8 was repeated except that neither the phenolic resin nor the shock-preventing agent was used. The viscosity, when the temperature became 10°C was 65 cp. In the step of dropping the 10% alkali, the viscosity at pH 7.0 was over 3,000 cp and the capsules aggregated.

Next, the same procedure as in Example 8 was repeated except that the phenolic resin was not added thereto. The viscosity at pH 7.9 during dropping of the alkali was 123 cp. and the amounts of gelatin deposited around the oil droplet at 10°C in the cases of Example 8 and Comparative Example 5 were 88%, 77% respectively, and the wall of the present invention was confirmed to be thicker than that realized in the Comparative Example.

EXAMPLE 9

In 20 parts of warm water at 35°C, 6 parts of acid-treated gelatin having an isoelectric point of 8.2 was dissolved.

Thereafter, 35 parts of liquid paraffin was emulsified to prepare an oil in water type emulsion. When the oil droplet became 20–25 μ in size, the stirring was stopped and 3 parts of gum arabic dissolved in 160 parts of warm water at 35°C was then poured therein, then the pH was adjusted to 4.2 by the dropwise addition of 10% hydrochloric acid with stirring the system. The contents were cooled, out of the vessel, with stirring to gel the colloid wall deposited. When the temperature of the system was 22°C during the cooling step, 5 parts of the phenolic rersin (60% resin content) obtained in Synthesis Example 2 was added. When the temperature of the system was 10°C, 20 parts of 10% sulfated cellulose sodium salt (degree of esterification: 0.74, viscosity at 25°C in 2% aqueous solution: 64 cp) was then added thereto and the cooling was continued and when the system temperature was 8° C, 3.0 parts of 37% formaldehyde was poured therein. The viscosity, at 10°C, was 18 cp.

Next, the pH was adjusted to 9.5 by the dropwise addition of a 10% caustic soda solution. The viscosity at pH 8.0 was 26 cp and the solution was heated to 45°C to obtain good heat-resistant single nucleus capsules containing fluid paraffin.

COMPARATIVE EXAMPLE 6

The same procedure as in Example 9 was repeated except that no phenolic resin was used. The viscosity of the resulting capsule solution was 67 cp at 10°C and that at pH 8.0 during changing the pH was 643 cp.

EXAMPLE 10

In 25 parts of warm water at 37°C, 6 parts of acid-treated gelatin having an isoelectric point of 7.8, 4 parts of gum arabic and 0.5 part of a styrene-maleic copolymer (Trade Name "Scripset" manufactured by Monsanto Chemical Company) were dissolved.

Then, 30 parts of lemon oil was emulsified. When the oil droplets in the water emulsion thus obtained became 20 to 25 μ in diameter, 170 parts of warm water at 35°C was poured therein. The pH was then adjusted to 4.5 with 10% sulfuric acid while stirring the system, and the contents were cooled, out of the vessel, to gel the wall formed. When the temperature was 12°C, 4 parts of phenolic resin (60% resin content) and subsequently 5 parts of 20% glutaldehyde were added thereto and cooled to 8°C.

Thereafter, 2 parts of 10% carboxymethylhydroxyethyl cellulose was added and the pH was adjusted to 9.2 by the dropwise addition of 10% caustic soda, then the contents were heated to 40°C to obtain capsules having a hardened wall.

The viscosity at 8°C during preparing the capsules was 38 cp and the viscosity at pH 8.0 was 67 cp.

EXAMPLE 11

6 Parts of acid-treated gelatin, 5 parts of gum arabic and 0.2 part of polyacrylic acid (Trade Name, "Aron 1OH", manufactured by Toa Gosei Chemical Industry Co., Ltd.) were dissolved in 30 parts of a polysulfide resin (Trade Name "Thiokol LP-32", manufactured by Thiokol Chem. Corp.) was emulsified so as to give emulsion droplets having a size of 50 μ. After adding 175 parts of warm water at 35°C thereto, 50% acetic acid was poured therein to adjust the pH of the system to 4.3. Thereafter, the contents were cooled, out of the vessel, with stirring thereof and when the temperature reached 25°C, 6 parts of the same compound as in Synthesis Example 4 were added thereto. When the temperature of the system was 8°C, 30 parts of a copolymer of potassium vinylbenzenesulfonate with morpholine (mole number of potassium vinylbenzenesulfonate: 76.5%, intrinsic viscosity measured in 1N·NaNO₃ at 30°C[n] = 0.421) was added thereto, and after 3 parts of 37% formaldehyde was poured therein, 10% caustic soda was added dropwise to adjust the pH to 9.5. The viscosity at pH 8.0 was 54 cp. By heating the system to 40°c, a Thiokol resin-containing capsule was obtained.

The capsules obtained were effectively used as capsules for a pressure-sensitive type adhesive.

COMPARATIVE EXAMPLE 7 except that no phenolic resin was employed.

The viscosity at pH 8.0 was 136 cp.

What is claimed is:

1. A process for producing oil-containing microcapsules by coacervation, which comprises:
    1. dispersing a hydrophobic fine powder or emulsifying a hydrophobic liquid into an aqueous solution of at least one type of high molecular weight electrolytic colloid for use in forming the capsule wall;
    2. subjecting dispersion or emulsion obtained in Step (1) to water dilution, and/or pH adjustment to achieve coacervation and optionally, adding an aqueous solution of a high molecular weight colloid, if desired;
    3. cooling the formed coacervate to gel the same;
    4. adding a phenolic compound thereto at a temperature above 5°C., during Steps (2) and (3);
    5. adding a hardening agent to the system;
    6. adding a shock-preventing agent to the system at a temperature lower than the gelling point of gelatin, said shock-preventing agent being capable of preventing a rapid increase in the viscosity of the system during pre-hardening of the coacervate when the pH of the system approaches a value of no less than about 6;
    7. adjusting the pH of the system to the alkali side, said Steps (5) through (7) constituting the pre-hardening treatment; and
    8. optionally elevating the temperature of the system to more effectively harden the coacervate, the order of Steps (5) through (7) being capable of being freely modified with respect to each other, and Step (5) further being capable of being conducted prior to Step (4), said shock-preventing agent being present in an amount sufficient to prevent a rapid increase in viscosity during pre-hardening, when the pH of the system approaches a value of no less than about 6 and being a member selected from the group consisting of

- a modified cellulose comprising polysaccharides having β-1,4-glucoside bonds of glucoses and having anionic functional groups,
- an anionic starch derivative composed of a linear polysaccharide amylose formed by only α-1,4-bonds of D-glucose, and a branched polysaccharide amylopectin formed by mainly α-1,4 bonds of D-glucose and a partially side chain branched by α-1,6 bonds,
- an anionic acid polysaccharide, obtained by poly-condensing linearly D-galacturonic acid between the α-1,4 bonds thereof, said acid polysaccharide containing pectin, pectic acid, and pectinic acid,
- a condensate of naphthalene sulfonic acid and Formalin, which condensate is represented by the formula:

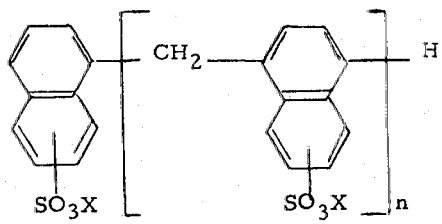

wherein X is a hydrogen atom, an alkali metal, or an ammonium group, and $n$ is a positive integer,

- a hydroxyethyl cellulose derivative selected from the group consisting of the carboxymethyl ether of hydroxyethyl cellulose, hydroxyethyl cellulose sulfate, and hydroxyethyl cellulose phosphate,
- a vinylbenzene sulfonate copolymer selected from the group consisting of a vinylbenzene sulfonate-acryloylmorpholine copolymer, a vinylbenzene sulfonate-morpholinoethylacrylamide copolymer, a vinylbenzene sulfonate acrylamide copolymer, a vinylbenzene sulfonate-vinylpyrrolidone copolymer, and a vinylbenzene sulfonatemethyloxy-methylacrylamide, said copolymer having the following group within its molecular structure:

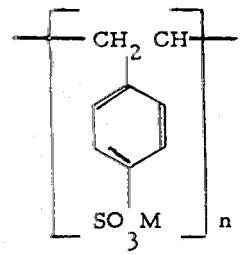

wherein M is an alkali metal and $n$ is a positive integer and, an acrylic acid copolymer selected from the group consisting of an acrylic acid-acryloylmorpholine copolymer, an acrylic acid-morpholinomethylacrylamide copolymer, an acrylic acid-acrylamide copolymer, an acrylic acid-vinylpyrrolidone copolymer, an acrylic acid-methoxymethylacrylamide copolymer, said copolymer having the following group within its molecular structure:

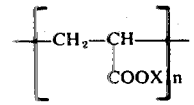

wherein X is a hydrogen atom or an alkali metal, and $n$ is a positive integer,
a maleic acid copolymer of maleic acid anhydride and at least one monomer having at least one unsaturated bond which is subjected to addition polymerization with said anhydride or a salt thereof, and a nucleic acid compound, said phenolic compound being present in an amount ranging from 1/500 to ¾ part by weight based on one part by weight of gelatin used to form the capsule wall, at least one of the hydrophilic colloids employed being gelatin.

2. The process of claim 1 where the coacervate is hardened between steps (7) and (8).

3. The process of claim 1, wherein said phenolic compound is a member selected from the group consisting of a phenol monomer and a phenol resin.

4. The process of claim 3, wherein said phenol monomer is an aromatic compound in which the hydrogen atom attached to the ring is substituted with at least one hydroxyl group.

5. The process of claim 4, wherein said phenolic monomer is a member selected from the group consisting of polyhydric phenols, phenolcarboxylic acids, nitrophenols and biphenols.

6. The process of claim 4, wherein said phenol monomer is a phenol compound having as a substituent a member selected from the group consisting of an alkyl group, an allyl group, a halogen atom, a halogen-substituted alkyl group, a cycloalkyl group, a phenyl group, a halogen-substituted phenyl group, an alkyl-substituted phenyl group, a biphenyl group, a benzyl group and a alpha-alkylbenzyl group.

7. The process of claim 4, wherein said phenol monomer is selected from the group consisting of o-cresol, m-cresol, p-cresol, o-ethylphenol, p-t-butylphenol, p-nonylphenol, p-dodecylphenol, p-octylphenol, p-fluoro-phenol, p-chlorophenol, p-bromophenol, m-chlorophenol, p-cyclohexylphenol, o-phenylphenol, p-phenylphenol, o-(o-chlorophenyl)-phenol, p-(p-bromophenyl)-phenol, o-(2-biphenylyl)-phenol, alpha-phenyl-o-cresol, 2,4-xylenol, 3,4-xylenol, 2-allyl-p-cresol, 2,4-dichlorophenol, 2,5-dichlorophenol, 4-chloro-m-cresol, 2-chloro-4-phenylphenol, 2,3,5-trimethylphenol, 2,3,5,6-tetramethylphenol, alpha-naphthol and beta-naphthol.

8. The process of 5, wherein said polyhyric phenol is a member selected from the group consisting of resorcinol, catechol, hydroquinone, pyrogallol, fluoroglucinol, 1,2-dihydroxy-4-methylbenzene, 1,3-dihydroxy-5-methylbenzene, 3,4-dihydroxy-1-methylbenzene, 3,5-dihydroxy-1-methylbenzene, 2,4-dihydroxyethyl-benzene, t-butylhydroxyquinone, 1,3-naphthalenediol, 1,4-naphthalenediol, 1,5-naphthalenediol, 1,6-naphthalenediol, 1,7-naphthalenediol, 4-phenylpyrocatechol, 4-chloroesorcinol, phenyl-hydroquinone, 4,6-dichloroesorcinol and tetrachorohydroquinone.

9. The process of claim 5, wherein said phenol carboxylic acid is a member selected from the group consisting of m-oxybenzoic acid, p-oxybenzoic acid, protocatechuic acid, alpha-resorcylic acid, beta-resorcylic acid, orsellinic acid, caffeic acid, umbellic acid and gallic acid.

10. The process of claim 5, wherein said nitrophenol is a member selected from the group consisting of p-nitrophenol, m-nitrophenol and o-nitrophenol.

11. The process of claim 5 wherein said biphenol is a member selected from the group consisting of biphenol, bicresol, dibenzylbiphenol, diethylbiphenol, dipropylbiphenol, diallylbiphenol, dihalobiphenol, diphenyltetrol, methylenediphenol, methylenebis (alkylphenol), methylenebis(benzylphenol), methylenebis(-phenylphenol) and methylenebis(halophenol).

12. The process of claim 5 wherein said biphenol is a member selected from the group consisting of o-o'-biphenol, m-m'-biphenol, p-p'-biphenol, 4,4'-bi-o-cresol, 4,4'-bi-m-cresol, 6,6'-o-cresol, 2,2'-diethyl-p-p'-biphenol, 2,2'-diallyl-p-p'-biphenol, 3,3'5,5'-biphenyltetrol, 4,4'-methylenediphenol, 2,4'-methylenediphenol, 2,2'-methylenediphenol, 4,4'-isopropylidenediphenol, 4,4'-cyclopentylidenephenol, 4,4'-cyclohexylidenediphenol, methylenediresorcinol, 4,4'-methylene-di-o-cresol, 4,4'-methylenebis(2-chlorophenol), 4,4'-methylenebis(2,5-dichlorophenol), and 4,4'-thiodiphenol.

13. The process of claim 3, wherein said phenol resin is a phenol-aldehyde resin.

14. The process of claim 13, wherein said phenol-aldehyde resin is water-soluble.

15. The process of claim 13, wherein said phenol of said phenolaldehyde resin is a member selected from the group consisting of phenol, cresol, xylenol, an alkylphenol and resorcinol.

16. The process of claim 13, wherein said aldehyde of said phenol-aldehyde resin is formaldehyde.

17. The process of claim 1, wherein said phenol compound is present in an amount ranging from 1/100 to ½ parts by weight based on one part by weight of colloid used to form the capsule wall.

18. The process of claim 1, wherein said colloid is a member selected from the group consisting of gelatin, casein, alginate, gum arabic, carrageenan, a maleic acid-styrene copolymer, a maleic acid-methylvinyl ether copolymer, and a maleic acid-ethylene copolymer.

19. The process of claim 1, wherein said phenolic compound is a resol-type or novolak-type phenolic resin.

* * * * *